US00PP16190P3

(12) United States Plant Patent
Bourne

(10) Patent No.: US PP16,190 P3
(45) Date of Patent: Jan. 10, 2006

(54) EUROPEAN PLUM TREE NAMED NAMED '92-110-69'

(50) Latin Name: *Prunus domestica*
Varietal Denomination: 92-110-69

(75) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 282 days.

(21) Appl. No.: 10/280,571

(22) Filed: Oct. 24, 2002

(65) Prior Publication Data

US 2004/0083508 P1 Apr. 29, 2004

(51) Int. Cl.
*A01H 5/00* (2006.01)

(52) U.S. Cl. ..... Plt./184

(58) Field of Classification Search ..... Plt./184, Plt./185

See application file for complete search history.

*Primary Examiner*—Howard J. Locker
(74) *Attorney, Agent, or Firm*—Jondle & Associates P.C.

(57) ABSTRACT

A new and distinct variety of European plum (*Prunus domestica*) is described herein. The new variety, which is self-fertile, ripens in mid-season with large, red-purple fruit and firm flesh, with a tendency to produce some double fruits. Ripened fruit attains a very high level of sugar and holds in cold storage very well.

1 Drawing Sheet

Genus and species: *Prunus domestica.*

BACKGROUND AND SUMMARY OF THE INVENTION

The invention described here is a new variety of plum, *Prunus domestica* cv. '92-110-69'. The seedling originates from a planned cross in 1993 in Tulare County, Calif. The new variety is characterized by having large, red-purple, elliptic fruits which ripen in early August in the Delano, Calif. area. The high quality fruit has firm texture, good storage characteristics, and is very sweet, making it suitable for the fresh market.

The emasculated seed parent was the variety 'Empress' (unpatented) and the pollen parent was the variety 'Moyer Perfecto' (unpatented). Seed from the planned cross was harvested in the summer of 1993, stratified, then planted in the spring of 1994 in Kern County near the city of McFarland, Calif. The original seedling tree was selected in 1997 and was then propagated by budding to a one-year old, nematode-resistant Myrobalan 29C rootstock (unpatended) in a two tree plot near McFarland, Calif. In 1999, a forty tree plot was propagated north of Delano, Calif. by cleft grating to two-year old, nematode-resistant Myrobalan 29C rootstock (unpatented) from wood of the two tree plot and the original seedling tree. Observations of trees from these propagations indicate that the characteristics are firmly fixed and all trees have proven true to type and identical to the original seedling tree.

COMPARISON WITH PARENTAL CULTIVAR

The new variety is intermediate in its characteristics between its two parents; fruits of the new variety are about the same size as 'Moyer Perfecto' fruits, but are more elongate like the fruits of 'Empress'. Fruit of the instant variety ripens about 2 weeks after 'Empress' and one week before 'Moyer Perfecto' in the Delano, Calif. area. As in the variety 'Empress', the new variety bears well on 2–3 year old trees before woody spurs develop on the scaffolds. This further distinguishes it from 'Moyer Perfecto' which does not bear well until the 5th or 6th year from planting with the development of spurs.

DESCRIPTION OF THE FIGURES

The accompanying photograph illustrates the following.

DETAILED BOTANICAL DESCRIPTION OF THE INVENTION

Figure 1:
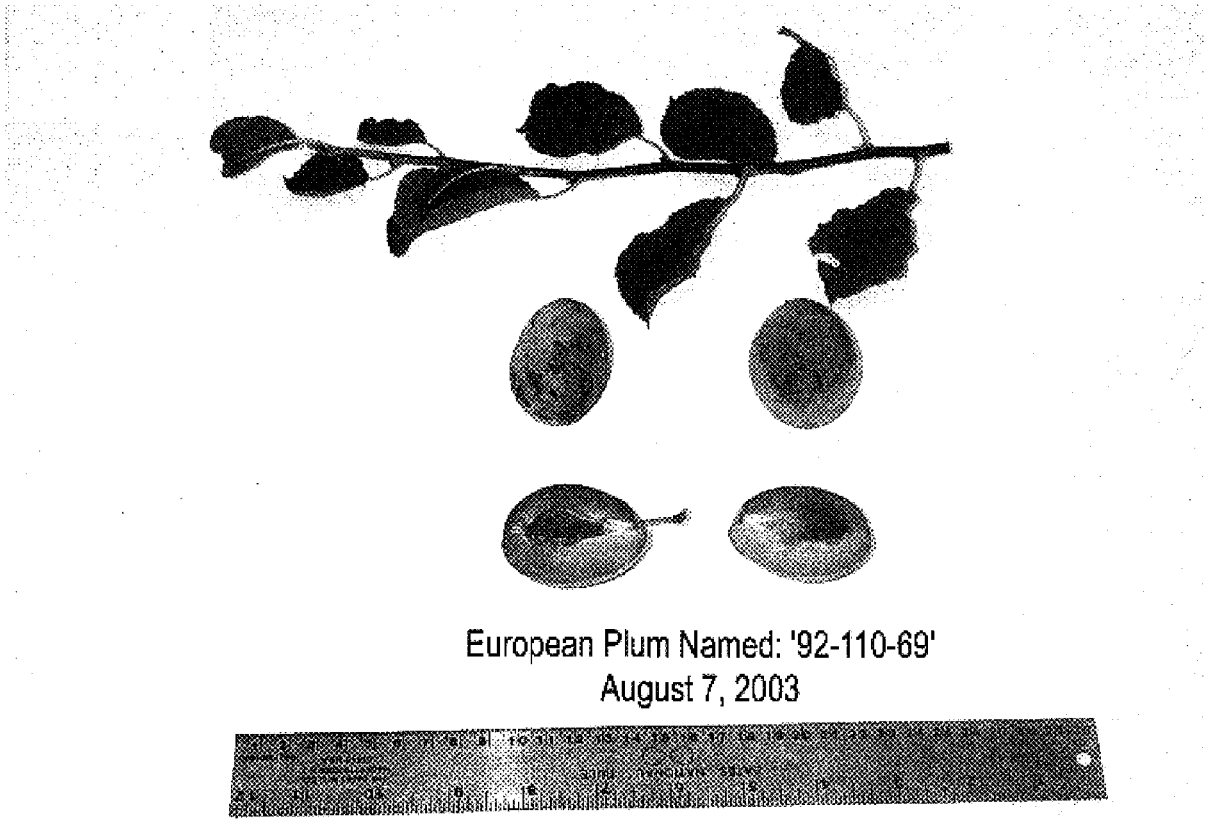
FIG. 1 shows the harvested fruit and a branch from the tree.

The following description of European Plum '92-110-69' contains references to color names taken from the Munsell Color Chart for Plant Tissues, published by Munsell Color, New Windsor, N.Y. The characteristics listed below were obtained from trees grown in the McFarland and Delano. Calif. area.

Tree:

*Habit.*—Upright.

*Productivity.*—Very good, sets excessively heavy crop requiring thinning.

*Rootstock.*—Myrobalan 29C (*Prunus cerasifera* Ehrh.) nematode-resistant rootstock.

Trunk:

*Seedling diameter.*—Seedling tree at 10 years in 0.6 mm×3 m row spacing=8.9 cm at 1.2 m height.

*Grafted tree diameter.*—Diameter at 30 cm height (6 year old trees at 2 m×3 m row spacing)=10.5 cm.

*Bark texture.*—Very rough.

*Trunk color.*—5YR 5/2 to 6/2 (grayish-brown).

*Trunk lenticel color.*—5YR 5/8 (orangish).

*Trunk lenticel length.*—4 mm.

*Trunk lenticel number.*—Variable. Large sectors with no lenticels to as many as 6 per sq.cm.

Branches:

*Size.*—Scaffold diameter of grafted trees (6 years old trees at 2 m×3 m row spacing), 45.7 cm above crotch=3.6 cm.

*Color.*—5YR 3/2 to 3/4.

*Lenticels.*—About 1 mm in diameter; approximately 36 per square cm.

*Lateral branching on first year branches.*—Uncommon.

*Length of mature, 1-year-old branches.*—150.5 cm.

Leaves:

*Blade length.*—8.5 cm.

*Blade width.*—5.5 cm.

*Petiole length.*—1.8 cm.

*Leaf shape.*—Obovate to elliptic.

*Leaf margins.*—Crenate, margins of upper surface cupped downward.

*Teeth.*—Both sides generally convex; about 2 mm in length.

*Upper surface color.*—7.5GY 4/4 to 4/6 (dark green).

*Lower surface color.*—7.5 GY 5/6 to 5/8 (dark green).

*Erect hairs on veins of lower surface.*—Numerous.

*Erect hairs on upper surface.*—Absent.

*Erect hairs on upper surface of petiole.*—Sparse.

Flowers:

*Date of first flowering near Delano, Calif.*—Mar. 15, 2004.

*Date of full bloom.*—Mar. 20, 2004.

*Date of last bloom.*—Mar. 26, 2004.

*Flower number per cluster.*—2–3.

*Bloom diameter.*—18 mm.

*Petal number.*—5.

*Petal color.*—Approximately 2.5GY 8/2 (white).

*Petal length.*—10 mm.

*Sepal color.*—5GY 5/10.

*Sepal number.*—5.

*Sepal length.*—7 mm.

*Flower type.*—Perfect, bearing both male and female organs.

*Anther number.*—About 30 per flower.

*Anther color.*—Yellow, 5Y 8/12.

*Carpels.*—1–2 per flower.

*Fertility.*—Self-fertile.

*Fragrance.*—Typical of European plums, faintly aromatic.

Fruit:

*Harvest maturity.*—Early mid-season.

*First harvest.*—Jul. 15, 2004.

*Last harvest.*—Jul. 22, 2004.

*Skin color with bloom.*—5RP 6/2 (reddish-purple).

*Skin color without bloom* (*undercolor*).—5RP 3/4.

*Flesh color.*—2.5Y 7/10 (yellow).

*Fruit length.*—4.6 cm.

*Fruit width.*—4.1 cm.

*Fruit size.*—Large, 52.2 g.

*Fruit stem length.*—19 mm.

*Fruit stem color.*—7.5GY 7.8.

*Refractometer test.*—23.2 brix.

*Pressure at harvest* (*penetrometer test*).—13.8 lbs.

*Configuration.*—Elliptic.

*Apex.*—Rounded.

*Pistil point.*—Smooth.

*Skin thickness.*—Thin, typical of European plum.

*Texture.*—Smooth.

*Tendency to crack.*—None.

*Fruit abnormalities.*—Some tendency to produce double fruit.

*Juiciness of flesh.*—Very juicy.

*Flavor.*—Mild and sweet, typical of European plum.

*Aroma.*—Mild.

*Texture.*—Crisp.

*Fibers.*—None.

*Ripening.*—Uniform throughout the fruit.

*Eating quality.*—Good.

*Use.*—Fresh market.

*Productivity.*—6-year-old trees grafted on Myrobalan 29C nematode-resistant rootstock (*Prunus cerasifera* Ehrh.) averaged 130.2 pounds of fruit per tree at 18×20 foot spacing. Seedling tree averaged 12.5 pounds of fruit growing in a seedling row at 2×10 foot spacing over 5 years.

*Keeping quality.*—Good, fruit holds well in storage for 4 weeks.

*Shipping quality.*—Good.

Stone:

*Stone adherence to flesh.*—Clingstone.

*Stone shape.*—Elliptic coming to a very fine point at apex.

*Fibers.*—None.

*Surface.*—Rough.

*Color.*—Brown: 5YR 5/8 to 5/10.

*Length.*—2.8 cm.

*Width.*—1.5 cm.

*Thickness.*—0.8 cm.

Disease resistance: Typical of European plums; no problems seen in growing trials or on seedling tree for 10 years period in the McFarland and Delano, Calif. areas.

What is claimed is:

1. A new and distinct variety of European Plum tree named '92-110-69' as herein described and illustrated, and identified by the characteristics enumerated above.

* * * * *